(12) United States Patent
Pless

(10) Patent No.: US 8,249,712 B2
(45) Date of Patent: Aug. 21, 2012

(54) TREATMENT AND WARNING OF RECURRING THERAPY AND OTHER EVENTS USING AN IMPLANTABLE DEVICE

(75) Inventor: Benjamin D Pless, Atherton, CA (US)

(73) Assignee: NeuroPace, Inc., Mountain View, CA (US)

( * ) Notice: Subject to any disclaimer, the term of this patent is extended or adjusted under 35 U.S.C. 154(b) by 0 days.

(21) Appl. No.: 13/293,476

(22) Filed: Nov. 10, 2011

(65) Prior Publication Data

US 2012/0059430 A1 Mar. 8, 2012

Related U.S. Application Data

(63) Continuation of application No. 11/490,818, filed on Jul. 21, 2006, now Pat. No. 8,073,545.

(51) Int. Cl.
*A61N 1/372* (2006.01)

(52) U.S. Cl. ............................................. 607/45; 607/46

(58) Field of Classification Search .................... 607/45, 607/46
See application file for complete search history.

(56) References Cited

U.S. PATENT DOCUMENTS

| | | | | |
|---|---|---|---|---|
| 6,006,124 A * | 12/1999 | Fischell et al. | ................. | 600/378 |
| 6,016,449 A * | 1/2000 | Fischell et al. | ................. | 607/45 |
| 6,473,639 B1 * | 10/2002 | Fischell et al. | ................. | 600/544 |
| 6,594,524 B2 * | 7/2003 | Esteller et al. | ................. | 607/45 |
| 6,810,285 B2 * | 10/2004 | Pless et al. | ..................... | 600/544 |
| 7,136,695 B2 * | 11/2006 | Pless et al. | ..................... | 600/544 |
| 7,149,572 B2 * | 12/2006 | Frei et al. | ....................... | 600/544 |
| 2002/0072770 A1 * | 6/2002 | Pless | .............................. | 607/2 |
| 2004/0133120 A1 * | 7/2004 | Frei et al. | ....................... | 600/544 |
| 2005/0107840 A1 * | 5/2005 | Conley et al. | .................... | 607/32 |
| 2006/0129204 A1 * | 6/2006 | Pless et al. | ....................... | 607/45 |

OTHER PUBLICATIONS http://www.siumed.edu/neuro/epilepsy/news/pressreleases/VNSpress.html (NeuroCybernetic Prosthesis (NCP) from Cyberonics, Inc.).*
http://www.medtronic.com/physician/activa/; http://www.medtronic.com/physician/activa/surg_components.html.*
Wagner, H.R., et al. "Suppression of Cortical Eplieptiform Activity by Generalized and Localized ECoG Desynchronization," Electroencephalogr. Clin. Neurophysiol. 1975: 39(5): 499-506.*
Weiland, J. D., et al., "Chronic Neural Stimulation With Thin-Film, Iridium Oxide Electrodes," IEEE Transactions on Biomedical Engineering, 74: 911-918 (2000).*

* cited by examiner

*Primary Examiner* — Scott Getzow
*Assistant Examiner* — Joseph Dietrich

(57) ABSTRACT

An implantable neurostimulator system is capable of responsively treating epileptiform activity with electrical stimulation and other therapies and is further configured to detect periods of increased susceptibility to clinical seizures. The event densities of therapy applications (or detections or other events) in time are observed and calculated, and if high enough, measures are taken to warn the patient or provide additional therapy.

14 Claims, 11 Drawing Sheets

TREATMENT AND WARNING OF RECURRING THERAPY AND OTHER EVENTS USING AN IMPLANTABLE DEVICE

RELATED APPLICATIONS

This application is a continuation application of U.S. patent application Ser. No. 11/490,818, now U.S. Pat. No. 8,073,545 filed Jul. 21, 2006, which is incorporated by reference herein in its entirety.

FIELD

The disclosure relates to systems and methods for detecting and treating epileptic seizures, and more particularly to detecting, treating, and providing notice of recurring epileptiform seizure-like activity and therapies delivered in a patient with epilepsy with an implantable device, wherein patterns of therapies may indicate increased susceptibility to seizures calling for further intervention or warning.

BACKGROUND

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

Electrical stimulation is an emerging therapy for epilepsy, and responsive therapy (i.e., therapy that is applied only when a device determines it is necessary or advantageous to do so) is at the cutting edge of electrical stimulation therapy.

Currently approved and available electrical stimulation devices apply continuous electrical stimulation to neural tissue surrounding or near implanted electrodes, and do not perform any detection—they are not responsive to relevant neurological conditions.

The NeuroCybemetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide substantial clinical benefit.

The Activa device from Medtronic is a pectorally implanted continuous deep brain stimulator intended primarily to treat Parkinson's disease. In operation, it supplies a continuous electrical pulse stream to a selected deep brain structure where an electrode has been implanted. Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

A typical epilepsy patient experiences episodic attacks or seizures, which are generally electrographically defined as periods of abnormal neurological activity. As is traditional in the art, such periods shall be referred to herein as "ictal". In many patients these ictal periods tend to cluster or occur in groups; at and around those times a patient is particularly prone to experience a seizure.

Seizure clusters are undesired for a number of reasons. Nearly all seizures, whether they involve loss of motor control, involuntary movements, or lapses of consciousness, are dangerous (both in a direct clinical sense and also as a result of accidents). Moreover, epilepsy is generally regarded as somewhat progressive, in that seizures tend to damage and degenerate already dysfunctional brain tissue. Seizure clusters may represent a particularly dysfunctional brain state, and when responsive therapy fails to adequately treat a patient, the progression of the disease may continue and the patient may be incapacitated over a particularly long period of time. This is true even if clinical symptoms are not evident.

Most work on the detection and responsive treatment of seizures via electrical stimulation has focused on analysis of electroencephalogram (EEG) and electrocorticogram (ECoG) waveforms. In common usage, the term "EEG" is often used to refer to signals representing aggregate neuronal activity potentials detectable via electrodes applied to a patient's scalp, though the term can also refer to signals obtained from deep in the patient's brain via depth electrodes and the like. Specifically, "ECoGs" refer to signals obtained from internal electrodes near the surface of the brain (generally on or under the dura mater); an ECoG is a particular type of EEG. Unless the context clearly and expressly indicates otherwise, the term "EEG" shall be used generically herein to refer to both EEG and ECoG signals, regardless of where in the patient's brain the electrodes are located.

It is best for a patient to avoid seizures entirely, but if that is not possible, it is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified and used to facilitate intervention before electrographic or clinical onsets occur. This capability would be considered seizure prediction, in contrast to the detection of a seizure or its onset.

U.S. Pat. No. 6,016,449 to Fischell, et al., for System for Treating Neurological Disorders (which is hereby incorporated by reference as though set forth in full herein), describes an implantable seizure detection and treatment system. In the Fischell system, various detection methods are possible, all of which essentially rely upon the analysis (either in the time domain or the frequency domain) of processed EEG signals. Fischell's controller is preferably implanted intracranially, but other approaches are also possible, including the use of an external controller. The processing and detection techniques applied in Fischell are generally well suited for implantable use. When a seizure is detected, the Fischell system applies responsive electrical stimulation to terminate the seizure, a capability that will be discussed in further detail below.

A more recent embodiment of seizure detecting device is described and claimed in U.S. Pat. No. 6,810,285 to Pless et al., also incorporated by reference as though set forth in full.

As is well known, it has been suggested that it is possible to treat and terminate seizures by applying electrical stimulation to the brain. See, e.g., U.S. Pat. No. 6,016,449 to Fischell et al., and H. R. Wagner, et al., Suppression of cortical epileptiform activity by generalized and localized ECoG desynchronization, Electroencephalogr. Clin. Neurophysiol. 1975; 39(5): 499-506. And it is postulated that a "stimulate early and often" strategy is advantageous. Observed epileptiform activity, even if it does not result in clinical symptoms, may be a subclinical seizure. Treatment of such subclinical activity may reduce overall seizure rates and reduce the brain's tendency to produce such activity in the future. In any event, reasonable quantities of "excess" stimulation have not been found to be disadvantageous.

Even when detection is operating effectively and an implantable system provides electrical stimulation therapy in response to electrographic events, and despite the suppression of those individual events, there may be times when the patient's brain is in a state of enhanced excitability and the rate of electrographic events increases. A responsive device, even when it is capable of applying therapy in response to individual electrographic events, might not be successful in keeping all of them from progressing to clinical seizures. Accordingly, it would be advantageous to have an implantable system for treating epilepsy that is capable of observing and responding to periods of increased activity and increased excitability, which is often manifested by a period of high therapy density (the system is treats multiple electrographic events in succession, yet they continue to occur). When a period of increased therapy activity is observed, it would be advantageous to be able to warn the patient to take protective measures or take in increased dose of an anticonvulsant medication, or to automatically provide additional therapy (above and beyond the responsive therapy already being applied) to reduce the impact or likelihood of a clinical seizure.

As is well known in the art, the computational ability of a processor-controlled system is directly related to both size and power consumption. In accordance with the above considerations, therefore, it would be advantageous to have sufficient detection and prediction capabilities to avoid a substantial number of false positive and false negative detections, and yet consume little enough power (in conjunction with the other subsystems) to enable long battery life. Such an implantable device would have a relatively low-power central processing unit to reduce the electrical power consumed by that portion.

As noted above, it has been observed that despite a high frequency of successful stimulations of electrographic events, there may be times when the numbers of electrographic events continues to increase resulting in an increased risk of a breakthrough seizure. This is true regardless of whether seizures are being treated with electrical stimulation as described above, and regardless of whether such treatments are successful on an individual basis (i.e. clinical symptoms are avoided). These observations suggest that there are times that can be identified by an increase in the amount of responsive stimulation delivered, when the patient's brain is highly excitable and conditions are particularly conducive to a seizure breakthrough. At these times, a patient's health and well-being may be particularly at risk.

At the current time, there is no known implantable device that is capable of detecting and responding to neurophysiological conditions suggestive of increased excitability and the possibility of a breakthrough seizure, or providing warnings or additional actions in response to a sequence of therapies having been applied.

SUMMARY

Accordingly, in various aspects, an implantable device for detecting epileptic seizures and responding to clusters of ictal episodes includes a relatively low-speed and low-power central processing unit, as well as customized electronic circuit modules in a detection subsystem. As described herein, the detection subsystem also performs prediction, which in the context of the present application is a form of detection that occurs before identifiable clinical symptoms or even obvious electrographic patterns are evident upon inspection. The same methods, potentially with different parameters, are adapted to be used for both detection and prediction. Generally, as described herein, a neurological event (such as an epileptic seizure) may be detected, an electrographic "onset" of such a neurological event (an electrographic indication of an event occurring at the same time as or before the clinical event begins) may be detected (and may be characterized by different waveform observations than the event itself), and a "precursor" to a neurological event (electrographic activity regularly occurring some time before the clinical event) may be detected as predictive of the neurological event.

Clusters of therapies in response to epileptiform activity, when detected and identified by a system in various aspects, can cause the device to provide warnings or other treatments to the patient. More specifically stated, when responsive therapy is applied repeatedly and undesired activity continues to occur (either in the form of epileptiform electrographic activity or clinical symptoms), the patient is deemed more susceptible to seizure breakthrough at that time, and the user can be warned to take preventive steps (such as to take additional medication) or further prophylactic electrical stimulation may be applied. In various aspects of a system, warnings and other messages to the patient may be provided by an audio transducer within the implanted device or via telemetry to a piece of external equipment, such as a personal computer.

As described herein and as the terms are generally understood, the present approach is generally not statistical or stochastic in nature. The detection subsystem thereof, is specifically adapted to perform much of the signal processing and analysis requisite for accurate and effective neurological event detection. The central processing unit remains in a suspended "sleep" state characterized by relative inactivity a substantial percentage of the time, and is periodically awakened by interrupts from the detection subsystem to perform certain tasks related to the detection and prediction schemes enabled by the device.

Much of the processing performed by an implantable system in various apsects involves operations on digital data in the time domain. Preferably, to reduce the amount of data processing used, samples at ten-bit resolution are taken at a rate less than or equal to approximately 500 Hz (2 ms per sample).

As stated above, an implantable system in various aspects is capable of accurate and reliable seizure detection and prediction. To accomplish this, the system employs a combination of signal processing and analysis modalities, including data reduction and feature extraction techniques, mostly implemented as customized digital electronics modules, minimally reliant upon a central processing unit.

Accordingly, in one embodiment, a system includes a central processing unit, as well as a detection subsystem that further includes a waveform analyzer. The waveform analyzer includes waveform feature analysis capabilities (such as half wave characteristics) as well as window-based analysis capabilities (such as line length and area under the curve), and both aspects are combined to provide enhanced neurological event detection. A central processing unit is used to consolidate the results from multiple channels and coordinate responsive action when necessary. Therapy, generally electrical stimulation, is provided by the system when neurological events are detected. The central processing unit is further programmed to identify sequences of therapies or other events, and in response thereto, to alert the patient that further seizures or undesired episodes are likely to occur. Provided with such information, the patient may take action (e.g. sit down in a safe location to avoid injury, administer medication, or call a caregiver).

The method is generally performed by analyzing electrographic signals with the line length, area, and half wave analysis tools described above, applying responsive therapy when appropriate, and employing software to identify patterns of delivered therapies. The process is relatively computationally efficient, in that dedicated hardware subsystems are employed where possible to reduce power consumption and allow the central processing unit to remain in a relatively low power state for as much time as possible.

BRIEF DESCRIPTION OF THE DRAWINGS

These and other objects, features, and advantages of the present invention will become apparent from the detailed description below and the accompanying drawings, in which.

DETAILED DESCRIPTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

As described above, a system is capable of detecting ictal activity and responding by applying responsive therapeutic electrical stimulation. In an embodiment, it is further capable of observing clusters of therapies, and when such clusters occur, triggering additional actions such as warning the patient or providing additional therapy.

Figure 1:
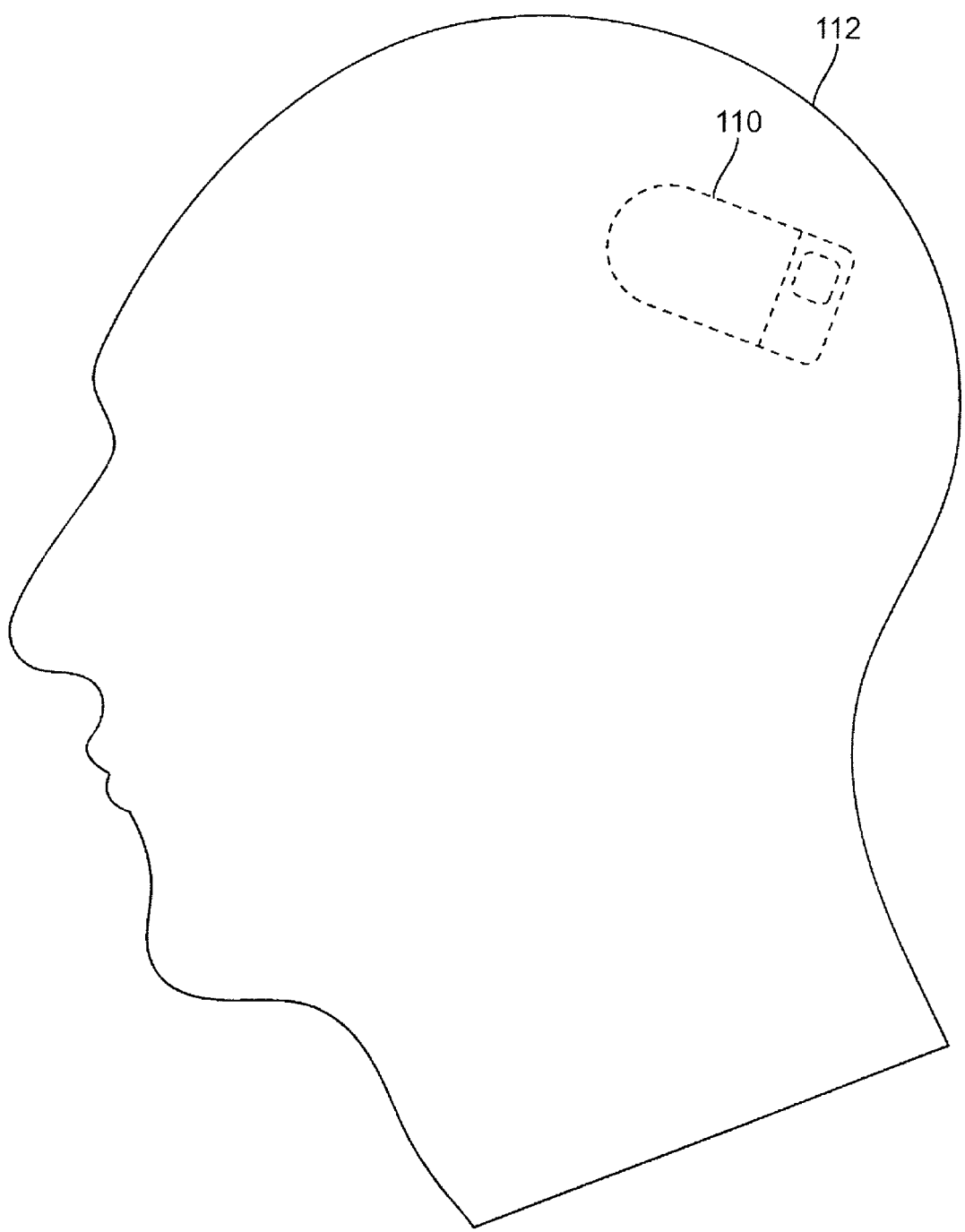
FIG. 1 is a schematic illustration of a patient's head showing the placement of an implantable neurostimulator according to an embodiment.

FIG. 1 depicts an intracranially implanted neurostimulator device 110, which in one embodiment is a small self-contained responsive neurostimulator located under the patient's scalp 112. As the term is used herein, a responsive neurostimulator is a device capable of detecting or predicting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects ictal activity by systems and methods in various embodiments.

Preferably, an implantable device in various embodiments is capable of detecting or predicting any kind of neurological event that has a representative electrographic signature. While the disclosed embodiment is described primarily as responsive to epileptic seizures, it should be recognized that it is also possible to respond to other types of neurological disorders, such as movement disorders (e.g. the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms begin.

Figure 2:
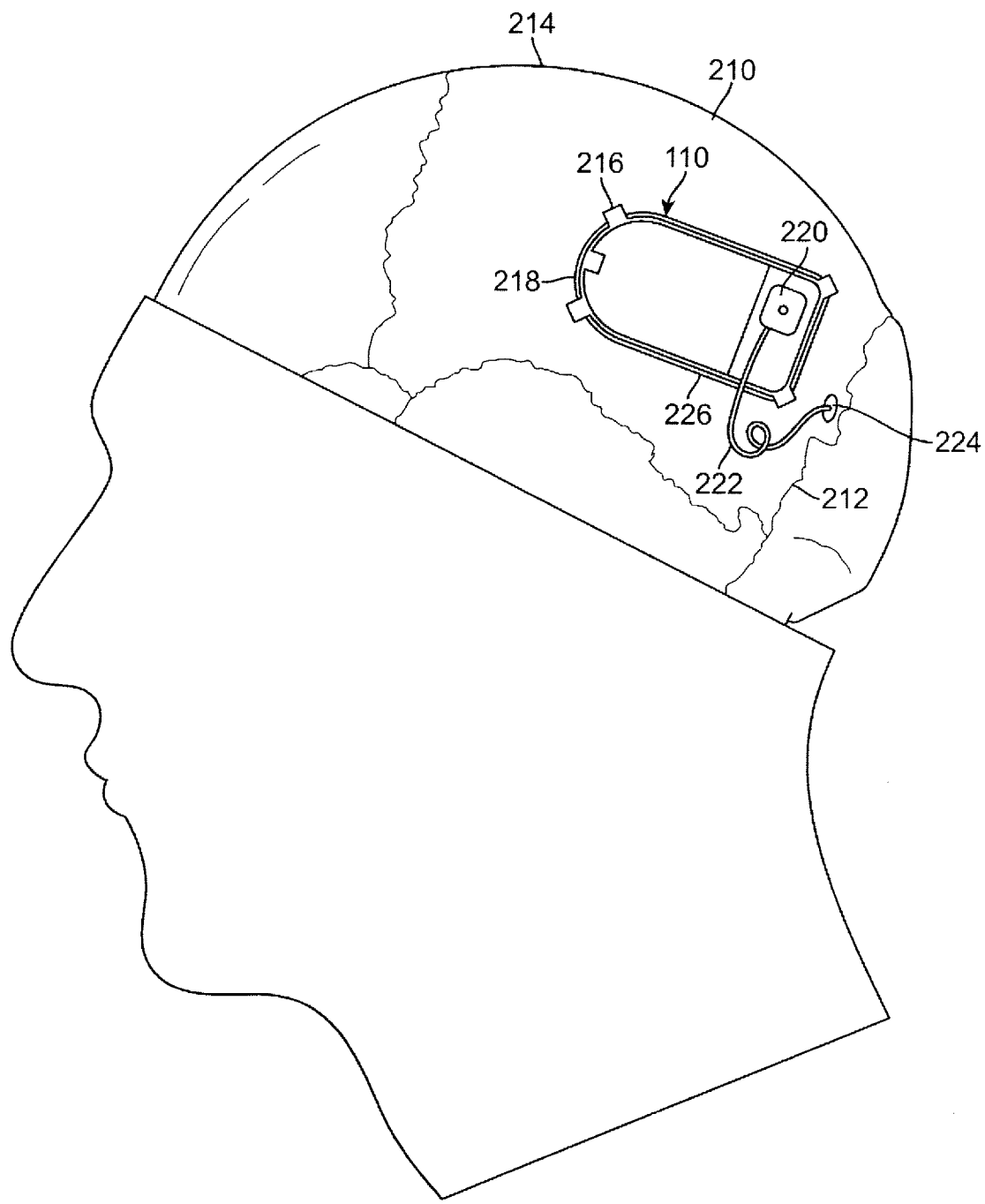
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoid suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patient's scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizures or their onsets or precursors, preventing and/or terminating such epileptic seizures, and responding to clusters of therapies as described herein.

In an alternative embodiment, the device 110 is not a responsive neurostimulator, but is an apparatus capable of detecting neurological conditions and events and performing actions in response thereto. The actions performed by such an embodiment of the device 110 need not be therapeutic, but may involve data recording or transmission, providing warnings to the patient, or any of a number of known alternative actions. Such a device will typically act as a diagnostic device when interfaced with external equipment, as will be discussed in further detail below.

The device 110, as implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone 210 anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (e.g., one of the sensors 412-418 of FIG. 4, in an embodiment in which the sensors are implemented as depth electrodes) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell, et al., for Means and Method for the Placement of Brain Electrodes, which is hereby incorporated by reference as though set forth in full herein, the burr hole 424 is sealed after implantation to prevent further movement of the lead 222; in an embodiment, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communication between the device 110 and external devices. Other portions of a system in various embodiments may also be positioned outside of the housing 226, as will be described in further detail below.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
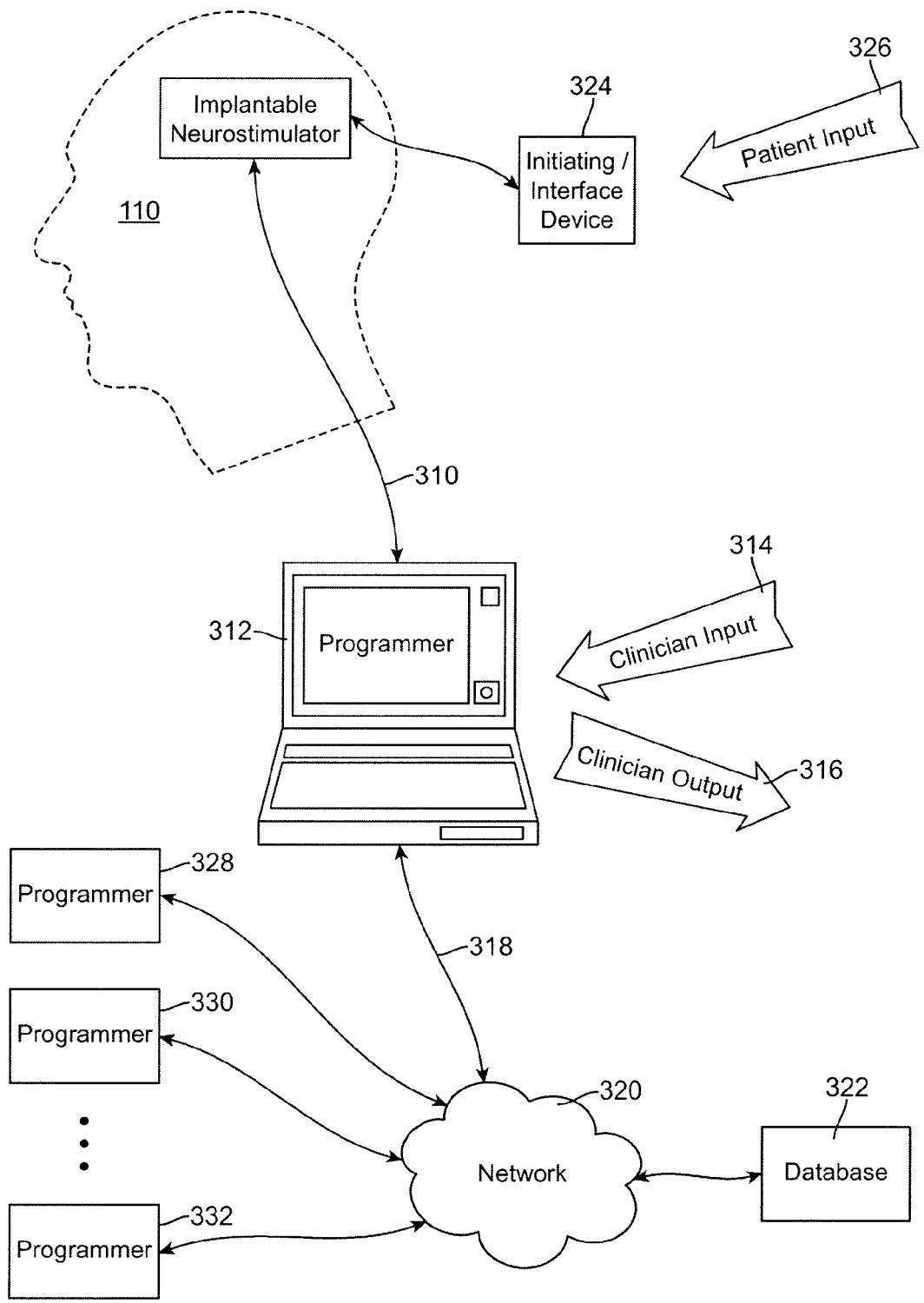
FIG. 3 is a block diagram illustrating a system context in which an implantable neurostimulator in an embodiment is implanted and operated.

As stated above, and as illustrated in FIG. 3, a neurostimulator in various embodiments operates in conjunction with external equipment. The implantable neurostimulator device 110 is mostly autonomous (particularly when performing its usual sensing, detection, and stimulation capabilities), but preferably includes a selectable part-time wireless link 310 to external equipment such as a programmer 312. In the disclosed embodiment, the wireless link 310 is established by moving a wand (or other apparatus) having communication capabilities and coupled to the programmer 312 into communication range of the implantable neurostimulator device 110. The programmer 312 can then be used to manually control the operation of the device, as well as to transmit information to or receive information from the implantable neurostimulator 110. Several specific capabilities and operations performed by the programmer 312 in conjunction with the device will be described in further detail below.

The programmer 312 is capable of performing a number of advantageous operations in connection with various embodiments. In particular, the programmer 312 is able to specify and set variable parameters in the implantable neurostimulator device 110 to adapt the function of the device to meet the patient's needs, upload or receive data (including but not limited to stored EEG waveforms, parameters, or logs of actions taken) from the implantable neurostimulator 110 to the programmer 312, download or transmit program code and other information from the programmer 312 to the implantable neurostimulator 110, or command the implantable neurostimulator 110 to perform specific actions or change modes as desired by a physician operating the programmer 312. To facilitate these functions, the programmer 312 is adapted to receive clinician input 314 and provide clinician output 316; data is transmitted between the programmer 312 and the implantable neurostimulator 110 over the wireless link 310.

The programmer 312 may be used at a location remote from the implantable neurostimulator 110 if the wireless link 310 is enabled to transmit data over long distances. For example, the wireless link 310 may be established by a short-distance first link between the implantable neurostimulator 110 and a transceiver, with the transceiver enabled to relay communications over long distances to a remote programmer 312, either wirelessly (for example, over a wireless computer network) or via a wired communications link (such as a telephonic circuit or a computer network).

The programmer 312 may also be coupled via a communication link 318 to a network 320 such as the Internet. This allows any information uploaded from the implantable neurostimulator 110, as well as any program code or other information to be downloaded to the implantable neurostimulator 110, to be stored in a database 322 at one or more data repository locations (which may include various servers and network-connected programmers like the programmer 312). This would allow a patient (and the patient's physician) to have access to important data, including past treatment information and software updates, essentially anywhere in the world where there is a programmer (like the programmer 312) and a network connection. Alternatively, the programmer 312 may be connected to the database 322 over a trans-telephonic link.

In yet another alternative embodiment, the wireless link 310 from the implantable neurostimulator 110 may enable a transfer of data from the neurostimulator 110 to the database 322 without any involvement by the programmer 312. In this embodiment, as with others, the wireless link 310 may be established by a short-distance first link between the implantable neurostimulator 110 and a transceiver, with the transceiver enabled to relay communications over long distances to the database 322, either wirelessly (for example, over a wireless computer network) or via a wired communications link (such as trans-telephonically over a telephonic circuit, or over a computer network).

In the disclosed embodiment, the implantable neurostimulator 110 is also adapted to receive communications from an initiating device 324, typically controlled by the patient or a caregiver. Accordingly, patient input 326 from the initiating device 324 is transmitted over a wireless link to the implantable neurostimulator 110; such patient input 326 may be used to cause the implantable neurostimulator 110 to switch modes (on to off and vice versa, for example) or perform an action (e.g., store a record of EEG data). Preferably, the initiating device 324 is able to communicate with the implantable neurostimulator 110 through a communication subsystem 430 (FIG. 4), and possibly in the same manner the programmer 312 does. The link may be unidirectional (as with the magnet and GMR sensor described below), allowing commands to be passed in a single direction from the initiating device 324 to the implantable neurostimulator 110, but in an alternative embodiment is bi-directional, allowing status and data (including warnings and alerts) to be passed back to the initiating device 324 for consideration by the patient or caregiver. Accordingly, the initiating device 324 may be a programmable PDA or other hand-held computing device, such as a Palm® device or PocketPC®. However, a simple form of initiating device 324 may take the form of a permanent magnet, if the communication subsystem 430 (FIG. 4) is adapted to identify magnetic fields and interruptions therein as communication signals.

The implantable neurostimulator 110 (FIG. 1) generally interacts with the programmer 312 (FIG. 3) as described below. Data stored in a memory subsystem 426 (FIG. 4) of the device 110 can be retrieved by the patient's physician through the wireless communication link 310, which operates through the communication subsystem 430 of the implantable neurostimulator 110. In connection with various embodiments, a software operating program run by the programmer 312 allows the physician to read out a history of neurological events detected including EEG information before, during, and after each neurological event, as well as specific information relating to the detection of each neurological event (such as, in one embodiment, the time-evolving energy spectrum of the patient's EEG). The programmer 312 also allows the physician to specify or alter any programmable parameters of the implantable neurostimulator 110. The software operating program also includes tools for the analysis and processing of recorded EEG records to assist the physician in developing optimized seizure detection parameters for each specific patient.

In an embodiment, the programmer 312 is primarily a commercially available PC, laptop computer, or workstation having a CPU, keyboard, mouse and display, and running a standard operating system such as Microsoft Windows®, Linux®, Unix®, or Apple Mac OS®. It is also envisioned that a dedicated programmer apparatus with a custom software package (which may not use a standard operating system) could be developed.

When running the computer workstation software operating program, the programmer 312 can process, store, play back and display on the display the patient's EEG or other sensor signals, as previously stored by the implantable neurostimulator 110 of the implantable neurostimulator device.

The computer workstation software operating program also has the capability to simulate the detection and prediction of abnormal electrical activity and other symptoms and results of chronic pain. Furthermore, the software operating program has the capability to allow a clinician to create or modify a patient-specific collection of information comprising, in one embodiment, algorithms and algorithm parameters for specific activity detection. The patient-specific collection of detection algorithms and parameters used for neurological activity detection will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator.

Following the development of a patient specific template on the programmer 312, the patient-specific template would be downloaded through the communications link 310 from the programmer 312 to the implantable neurostimulator 110.

The patient-specific template is used by a detection subsystem 422 and CPU 428 (FIG. 4) of the implantable neurostimulator 110 to detect conditions indicating treatment should be administered, and can be programmed by a clinician to result in responsive stimulation of the patient's brain, as well as the storage of EEG records before and after the detection, facilitating later clinician review.

Preferably, the database 322 is adapted to communicate over the network 320 with multiple programmers, including the programmer 312 and additional programmers 328, 330, and 332. It is contemplated that programmers will be located at various medical facilities and physicians' offices at widely distributed locations. Accordingly, if more than one programmer has been used to upload EEG records from a patient's implantable neurostimulator 110, the EEG records will be aggregated via the database 322 and available thereafter to any of the programmers connected to the network 320, including the programmer 312.

Figure 4:
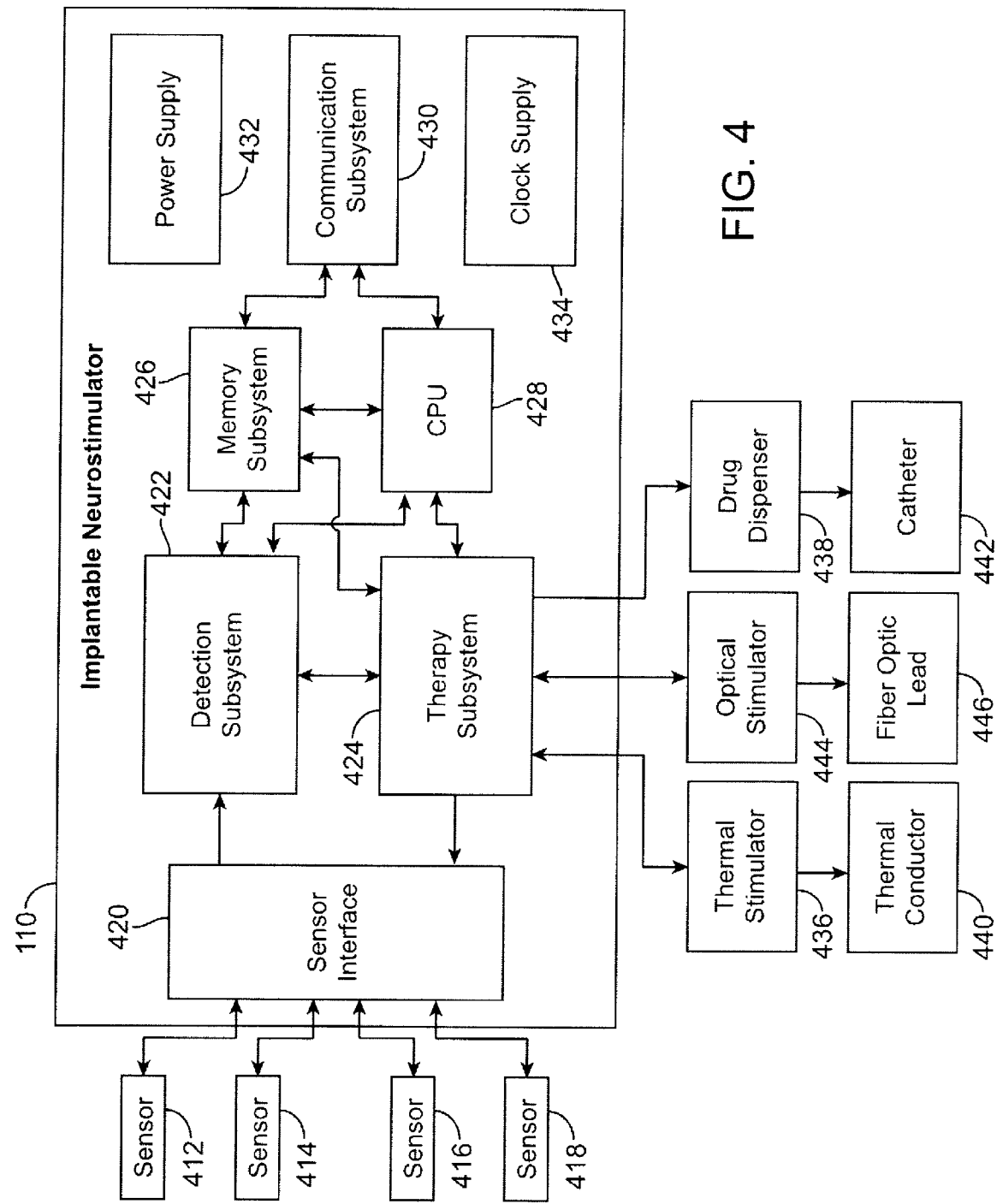
FIG. 4 is a block diagram illustrating the major functional subsystems of an implantable neurostimulator.

FIG. 4 is an overall block diagram of the implantable neurostimulator device 110 used for measurement, detection, and treatment in various embodiments. Inside the housing of the neurostimulator device 110 are several subsystems making up the device. The implantable neurostimulator device 110 is capable of being coupled to a plurality of sensors 412, 414, 416, and 418 (each of which may be individually or together connected to the implantable neurostimulator device 110 via one or more leads), which in an embodiment are electrodes used for both sensing and stimulation as well as the delivery of other treatment modalities. In the illustrated embodiment, the coupling is accomplished through a lead connector.

Although four sensors are shown in FIG. 4, it should be recognized that any number is possible, and in an embodiment described in detail herein, eight electrodes are used as sensors. In fact, it is possible to employ an embodiment that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise. In an alternative embodiment, electrodes are used in combination with other sensors, such as temperature and blood flow sensors, as will be described below.

The sensors 412-418 are in contact with the patient's brain or are otherwise advantageously located to receive EEG signals or provide electrical stimulation or another therapeutic modality. In an embodiment, one or more of the sensors 412-418 can be an electrochemical sensor, a temperature sensor, or any of a number of sensor types capable of measuring cerebral blood flow, oxygenation, or any other local physiological condition of interest. See U.S. Pat. No. 7,341,562 to Pless et al., and entitled "Modulation and analysis of cerebral perfusion in epilepsy and other neurological disorders," which is hereby incorporated by reference as though set forth in full herein.

Each of the sensors 412-418 is electrically coupled to a sensor interface 420. Preferably, the sensor interface is capable of selecting electrodes as required for sensing and stimulation; accordingly the sensor interface is coupled to a detection subsystem 422 and a therapy subsystem 424 (which, in various embodiments, may provide electrical stimulation and other therapies). The sensor interface 420 may also provide any other features, capabilities, or aspects, including but not limited to amplification, isolation, and charge-balancing functions, that are required for a proper interface with neurological tissue and not provided by any other subsystem of the device 110.

In an embodiment in which electrographic signals are received by electrodes and analyzed, the detection subsystem 422 includes and serves primarily as an EEG waveform analyzer. It will be recognized that similar principles apply to the analysis of other types of waveforms received from other types of sensors. Detection is generally accomplished in conjunction with a central processing unit (CPU) 428. The waveform analyzer function is adapted to receive signals from the sensors 412-418, through the sensor interface 420, and to process those EEG signals to identify abnormal neurological activity characteristic of a disease or symptom thereof. One way to implement such EEG analysis functionality is disclosed in detail in U.S. Pat. No. 6,016,449 to Fischell et al., incorporated by reference above. Additional inventive methods are described in U.S. Pat. No. 6,810,285 to Pless et al., of which relevant details will be set forth below (and which is also hereby incorporated by reference as though set forth in full). The detection subsystem may optionally also contain further sensing and detection capabilities, including but not limited to parameters derived from other physiological conditions (such as electrophysiological parameters, temperature, blood pressure, neurochemical concentration, etc.). In general, prior to analysis, the detection subsystem performs amplification, analog to digital conversion, and multiplexing functions on the signals in the sensing channels received from the sensors 412-418.

The therapy subsystem 424 is capable of applying electrical stimulation or other therapies to neurological tissue. This can be accomplished in any of a number of different manners. For example, it may be advantageous in some circumstances to provide stimulation in the form of a substantially continuous stream of pulses, or on a scheduled basis. In an embodiment, scheduled therapy (such as stimulation via biphasic pulses or other waveforms, such as low-frequency sine waves) can be performed by the device 110 in addition to and independent of responsive therapy. Preferably, therapeutic stimulation is provided in response to abnormal neurological events or conditions detected by the waveform analyzer function of the detection subsystem 422. As illustrated in FIG. 4, the therapy subsystem 424 and the EEG analyzer function of the detection subsystem 422 are in communication; this facilitates the ability of therapy subsystem 424 to provide responsive electrical stimulation and other therapies, as well as an ability of the detection subsystem 422 to blank the amplifiers while electrical stimulation is being performed to minimize stimulation artifacts. It is contemplated that the parameters of a stimulation signal (e.g., frequency, duration, waveform) provided by the therapy subsystem 424 would be specified by other subsystems in the implantable device 110, as will be described in further detail below.

The therapy subsystem 424 may also provide for other types of stimulation, besides electrical stimulation described above. In particular, in certain circumstances, it may be advantageous to provide audio, visual, or tactile signals to the patient, to provide somatosensory electrical stimulation to locations other than the brain, or to deliver a drug or other therapeutic agent (either alone or in conjunction with stimulation). Any of these therapies can be provided in a non-responsive therapy modality, such as scheduled therapy, either alone or in combination with a responsive therapy regimen.

Also the implantable neurostimulator device 110 contains a memory subsystem 426 and the CPU 428, which can take the form of a microcontroller. The memory subsystem is coupled to the detection subsystem 422 (e.g., for receiving and storing data representative of sensed EEG or other signals and evoked responses), the therapy subsystem 424 (e.g., for providing stimulation waveform parameters to the therapy subsystem for electrical stimulation), and the CPU 428, which can control the operation of (and store and retrieve data from) the memory subsystem 426. In addition to the memory subsystem 426, the CPU 428 is also connected to the detection subsystem 422 and the therapy subsystem 424 for direct control of those subsystems.

Also provided in the implantable neurostimulator device 110, and coupled to the memory subsystem 426 and the CPU 428, is a communication subsystem 430. The communication subsystem 430 enables communication between the device 110 and the outside world, particularly the external programmer 312 and initiation device, i.e. patient interface device 324, both of which are described above with reference to FIG. 3. As set forth above, the disclosed embodiment of the communication subsystem 430 includes a telemetry coil (which may be situated outside of the housing of the implantable neurostimulator device 110) enabling transmission and reception of signals, to or from an external apparatus, via inductive coupling. Alternative embodiments of the communication subsystem 430 could use an antenna for an RF link or an audio transducer for an audio link. Preferably, the communication subsystem 430 also includes a GMR (giant magnetoresistive effect) sensor to enable receiving simple signals (namely the placement and removal of a magnet) from a patient interface device; this capability can be used to initiate EEG recording as will be described in further detail below.

For an implantable device, it is reasonable to expect RF communication ranges of up to a few meters, possibly more. In an embodiment, a long-range telemetry RF link operates in the MICS (Medical Implant Communications Service) band at approximately 402-405 MHz. This band is well suited for communication within and around the human body and is available for use in the United States without a license.

Several support components are present in the implantable neurostimulator device 110, including a power supply 432 and a clock supply 434. The power supply 432 supplies the voltages and currents necessary for each of the other subsystems. The clock supply 434 supplies substantially all of the other subsystems with any clock and timing signals necessary for their operation, including a real-time clock signal to coordinate programmed and scheduled actions and the timer functionality used by the detection subsystem 422 that is described in detail below.

In an embodiment, the therapy subsystem 424 is coupled to a thermal stimulator 436 and a drug dispenser 438, thereby enabling therapy modalities other than electrical stimulation. These additional treatment modalities will be discussed further below. Respectively, the thermal stimulator 436 and the drug dispenser 438 are coupled to respective outputs, a thermal conductor 440 and a catheter 442, positioned at a desired location. Any of the therapies delivered by the therapy subsystem 424 is delivered to a therapy output at a specific site; it will be recognized that the therapy output may be a stimulation electrode, a drug dispenser outlet, or a thermal stimulation site (e.g. Peltier junction or thermocouple) as appropriate for the selected modality.

The therapy subsystem 424 is further coupled to an optical stimulator 444 and a fiber optic lead 446, enabling optical stimulation of neural structures in the brain, spinal cord, and nerves. Generally, the optical stimulator 444 includes a controllable light emitter (such as at least one LED or laser diode) that is situated onboard or in close proximity to the device 110, and the light is transmitted to the stimulation site via the fiber optic lead 446. One or more lenses may be used at the proximal or distal ends of the fiber optic lead 446 to increase light collection from the emitter (at the proximal end) and to focus the optical stimulation (at the distal end). It is understood that optical stimulation intensity is a function of both wavelength and intensity; different patients and different targets will react differently to different light colors, intensities, stimulation pulse widths, and stimulation burst durations (where pulse trains are delivered).

It should be observed that while the memory subsystem 426 is illustrated in FIG. 4 as a separate functional subsystem, the other subsystems may also require various amounts of memory to perform the functions described above and others. Furthermore, while the implantable neurostimulator device 110 is preferably a single physical unit (i.e., a control module) contained within a single implantable physical enclosure, namely the housing described above, other embodiments might be configured differently. The neurostimulator 110 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described above may be performed by electronic hardware, computer software (or firmware), or a combination thereof. The division of work between the CPU 428 and the other functional subsystems may also vary—the functional distinctions illustrated in FIG. 4 may not reflect the partitioning and integration of functions in a real-world system or method in various embodiments.

Figure 5:
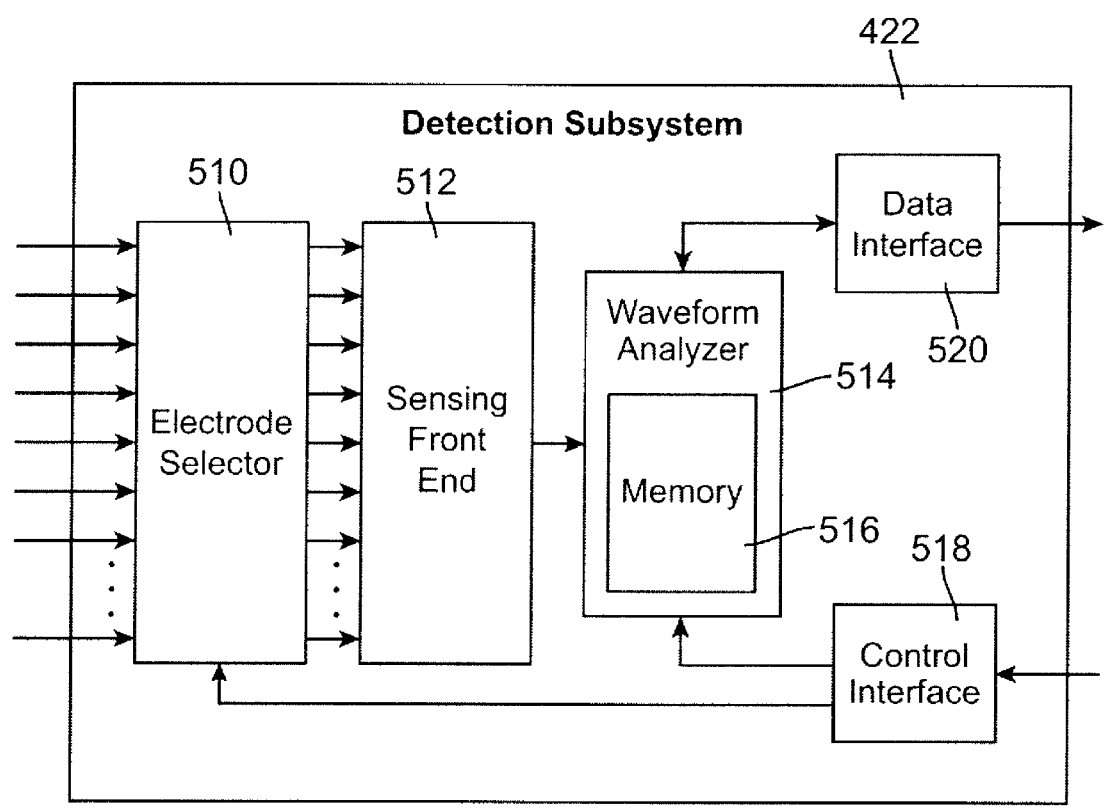
FIG. 5 is a block diagram illustrating the functional components of the detection subsystem of the implantable neurostimulator shown in FIG. 4.

FIG. 5 illustrates details of the detection subsystem 422 (FIG. 4). Inputs from the sensors 412-418 are on the left, and connections to other subsystems are on the right.

Signals received from the electrodes 412-418 (as routed through the electrode interface 420) are received in an electrode selector 510. The electrode selector 510 allows the device to select which electrodes (of the electrodes 412-418) should be routed to which individual sensing channels of the detection subsystem 422, based on commands received through a control interface 518 from the memory subsystem 426 or the CPU 428 (FIG. 4). Preferably, each sensing channel of the detection subsystem 422 receives a bipolar signal representative of the difference in electrical potential between two selectable electrodes. Accordingly, the electrode selector 510 provides signals corresponding to each pair of selected electrodes (of the electrodes 412-418) to a sensing front end 512, which performs amplification, analog to digital conversion, and multiplexing functions on the signals in the sensing channels. The sensing front end will be described further below in connection with FIG. 6.

A multiplexed input signal representative of all active sensing channels is then fed from the sensing front end 512 to a waveform analyzer 514. The waveform analyzer 514 is preferably a special-purpose digital signal processor (DSP) adapted for use in an embodiment, or in an alternative embodiment, may comprise a programmable general-purpose DSP. In the disclosed embodiment, the waveform analyzer has its own scratchpad memory area 516 used for local storage of data and program variables when the signal processing is being performed. In either case, the signal processor performs suitable measurement and detection methods described generally above and in greater detail below. Any results from such methods, as well as any digitized signals intended for storage transmission to external equipment, are passed to various other subsystems of the neurostimulator device 110, including the memory subsystem 426 and the CPU 428 (FIG. 4) through a data interface 520. Similarly, the control interface 518 allows the waveform analyzer 514 and the electrode selector 510 to be in communication with the CPU 428.

Figure 6:
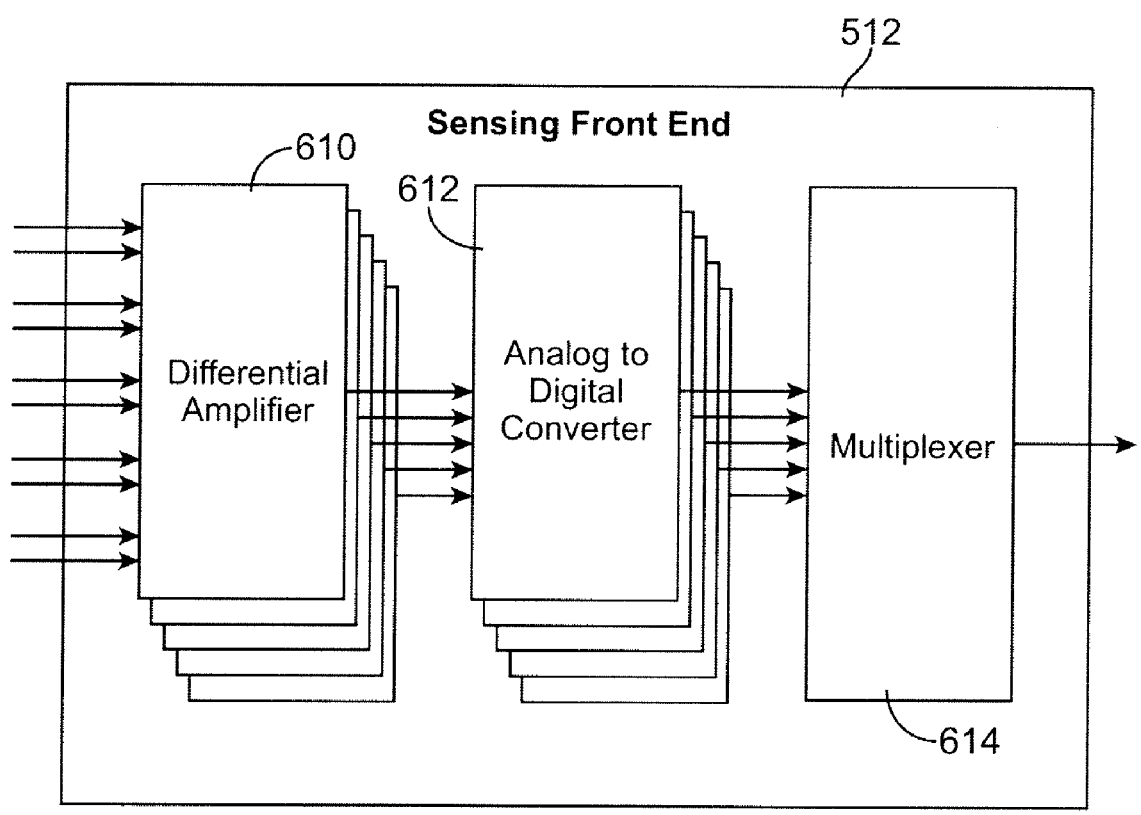
FIG. 6 is a block diagram illustrating the functional components of the sensing front end of the detection subsystem of FIG. 5.

Referring now to FIG. 6, the sensing front end 512 (FIG. 5) is illustrated in further detail. As shown, the sensing front end includes a plurality of differential amplifier channels 610, each of which receives a selected pair of inputs from the electrode selector 510. In an embodiment, each of differential amplifier channels 610 is adapted to receive or to share inputs with one or more other differential amplifier channels 610 without adversely affecting the sensing and detection capabilities of a system in various embodiments. Specifically, in an embodiment, there are at least eight electrodes, which can be mapped separately to eight differential amplifier channels 610 representing eight different sensing channels and capable of individually processing eight bipolar signals, each of which represents an electrical potential difference between two monopolar input signals received from the electrodes and applied to the sensing channels via the electrode selector 510. For clarity, only five channels are illustrated in FIG. 6, but it should be noted that any practical number of sensing channels may be employed in a system in various embodiments.

Each differential amplifier channel 610 feeds a corresponding analog to digital converter (ADC) 612. Preferably, the analog to digital converters 612 are separately programmable with respect to sample rates—in the disclosed embodiment, the ADCs 612 convert analog signals into 10-bit unsigned integer digital data streams at a sample rate selectable between 250 Hz and 500 Hz. In several of the illustrations described below where waveforms are shown, sample rates of 250 Hz are typically used for simplicity. However, the invention shall not be deemed to be so limited, and numerous sample rate and resolution options are possible, with tradeoffs known to individuals of ordinary skill in the art of electronic signal processing. The resulting digital signals are received by a multiplexer 614 that creates a single interleaved digital data stream representative of the data from all active sensing channels. As will be described in further detail below, not all of the sensing channels need to be used at one time, and it may in fact be advantageous in certain circumstances to deactivate certain sensing channels to reduce the power consumed by a system in various embodiments.

It should be noted that as illustrated and described herein, a "sensing channel" is not necessarily a single physical or functional item that can be identified in any illustration. Rather, a sensing channel is formed from the functional sequence of operations described herein, and particularly represents a single electrical signal received from any pair or combination of electrodes, as preprocessed by a system according to the invention, in both analog and digital forms. See, e.g., U.S. Pat. No. 6,473,639 to D. Fischell et al., entitled "Neurological Event Detection Using Processed Display Channel Based Algorithms and Devices Incorporating These Procedures," which is hereby incorporated by reference as though set forth in full herein. At times (particularly after the multiplexer 614), multiple sensing channels are processed by the same physical and functional components of the system; notwithstanding that, it should be recognized that unless the description herein indicates to the contrary, a system in various embodiments, handles, and treats each sensing channel independently.

In an embodiment, each time a responsive therapy is applied by a system in various embodiments, the time of the therapy event is stored in a buffer. This stored information is used in the software process illustrated in FIG. 7, which is performed on a periodic basis, preferably once every processing window (a recurring time interval that is either fixed or programmable) by a system in various embodiments. This software process enables action to be taken when therapy (or other event) densities exceed a programmed threshold, for example to warn a patient or provide additional therapy when a cluster of therapies is identified. Consistent with the other analysis tools described herein, the duration of an exemplary processing window is in one embodiment 128 ms. For purposes of this description, an application of responsive therapy is deemed an "event," thereby enabling warnings or further therapy when the patient's condition does not respond to repeated therapies, but other types of events, such as seizure onset detections, may also be used.

Figure 7:
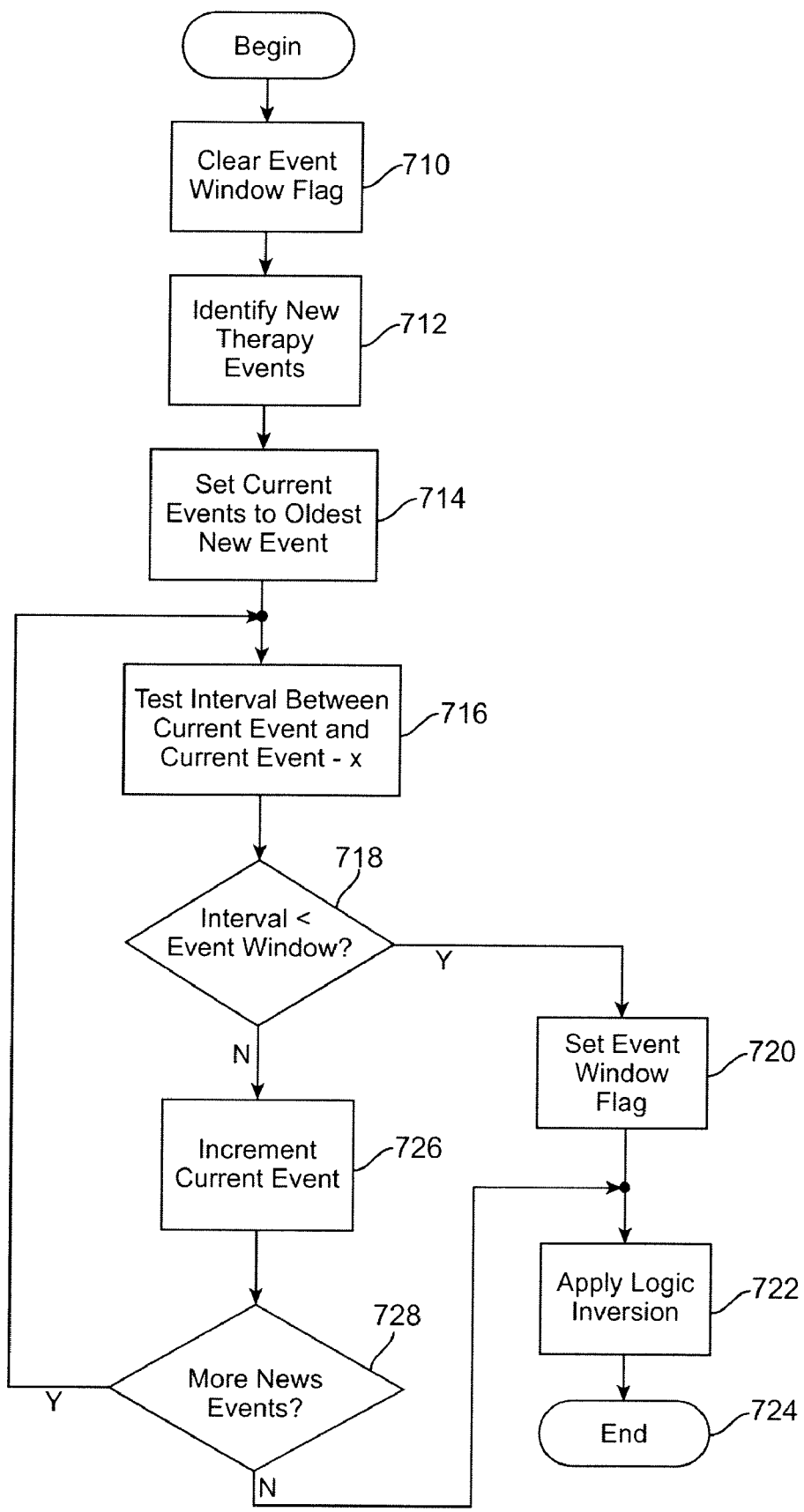
FIG. 7 is a flow chart illustrating the steps performed in identifying clusters of events in an embodiment.

Each time the software process of FIG. 7 is invoked, an event window flag is first cleared (step 710). Any therapy events that are newly identified since the last invocation of the procedure (i.e., all therapy events that occurred within the preceding processing window) are identified (step 712). A "current event" pointer is set to point to the oldest event identified in the most recent processing window (step 714). The time interval between the current event and the prior x events is then measured (step 716), where x is a specified minimum number of events (preferably a programmable value) to be identified within a selected event time window (the duration of which is another programmable value) to result in the possible detection of a neurological event. If the time interval is less than the duration of the event time window (step 718), then the event window flag is set (step 720), logic inversion is selectively applied (step 722), and the procedure ends (step 724). Logic inversion, a mechanism for determining whether an analysis unit is triggered by the presence or absence of a condition, is explained in greater detail below. Otherwise, the current event pointer is incremented to point to the next new event (step 728), and if there are no more new events (step 730), logic inversion is applied if desired (step 722), and the procedure ends (step 724). Otherwise, the next time interval is tested (step 716) and the process continues from there.

Logic inversion allows the output flag for the therapy event detector (or any other analyzer) to be selectively inverted. If logic inversion is configured to be applied, then the corresponding flag will be clear when the detection criterion (e.g., sufficient density of therapy events) is met, and set when the detection criterion is not met. This capability provides some additional flexibility in configuration, facilitating detection of the absence of certain signal characteristics when, for example, the presence of those characteristics is the norm.

In an embodiment, the event window flag (set in step 720) indicates whether a sufficient number of therapy events (or alternatively, as set forth above, detection events or any other event of interest) occur over an interval ending in the most recent processing window. An X of Y criterion may also be applied, causing the event density detector to trigger only if a sufficient number of events occurred in X of the Y most recent processing windows, where X and Y are programmable parameters.

Figure 8:
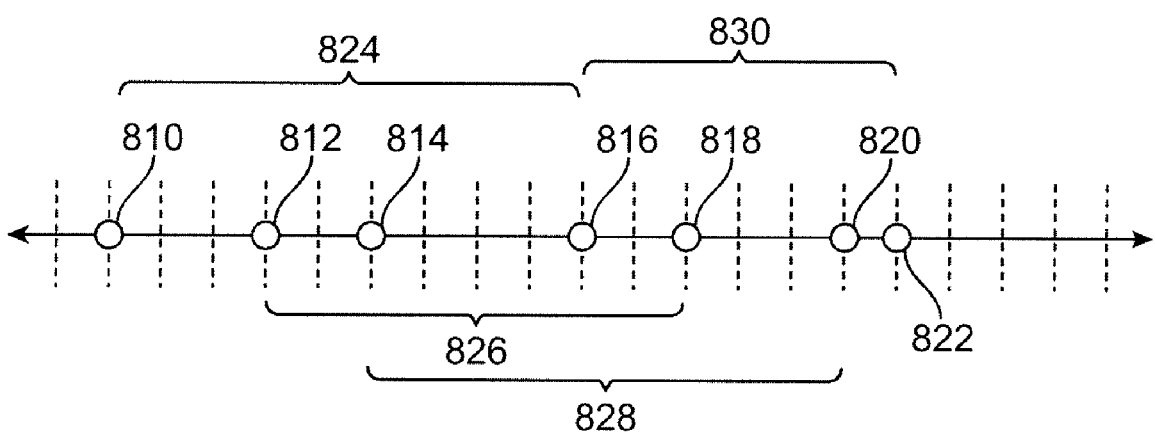
FIG. 8 is a time strip diagram illustrating several events over the course of time and providing an example of how event densities are calculated.

An illustration is provided in FIG. 8. A sequence of seven events 810, 812, 814, 816, 818, 820, and 822, each of which represents an application of responsive stimulation, takes place over a time scale; in the illustration, each vertical hash mark marks an interval of 20 seconds. In an embodiment, and purely for illustration, each of the events 810-822 represents a responsive therapy delivered by the device 110 system in various embodiments (generally following a detection of epileptiform activity); they are depicted at exact 20-second intervals solely for clarity. As set forth above, when each responsive therapy is delivered, its time is stored in a buffer.

To summarize the detection of event clusters, every time a therapy event occurs, the time interval between that event (event N) and a previous event (event N-x, where x is the threshold number of events within a certain time period, as described above) is measured. If that interval is small enough, an action is performed. In the example of FIG. 8, the threshold number of events is four (x=4), while the limiting time period is 140 seconds. These numbers are chosen for simplicity in explanation and illustration; in a clinically effective embodiment, other thresholds will apply and would generally be programmable by a clinician on a patient-specific basis.

As illustrated in FIG. 8, because the minimum number of events is four, after the fourth event 816, a first interval 824 between the fourth event 816 and the first event 810 is measured. The first interval 824 has a duration of nine twenty-second epochs or 180 seconds, so the density criterion is not satisfied. After the fifth event 818, a second interval 826 is measured, and it has a duration of eight epochs or 160 seconds; again the density criterion is not satisfied. After the sixth event 820, a third interval 828 is measured, and it has a duration of nine epochs or 180 seconds; this does not satisfy the event density criterion. Finally, after the seventh therapy event 822, a fourth interval 830 is measured, and it has a duration of six epochs or 120 seconds. It will be recognized that the duration of the fourth interval 830 is shorter than the maximum selected time period of 140 seconds, and accordingly a device in various embodiments triggers a warning, intervention, the application of prophylactic therapy, or some other action in response thereto.

The meta-detection scheme set forth herein is power efficient; intervals only need to be calculated for time epochs following the application of therapy events (or other selected events). At all other times, no additional processing needs to occur.

Cluster density analysis as described herein can also be combined advantageously with other detection tools in a system. For example, it may be advantageous in an embodiment to determine when therapies are being repeatedly applied and certain types of signal activities are high simultaneously.

Figure 9:
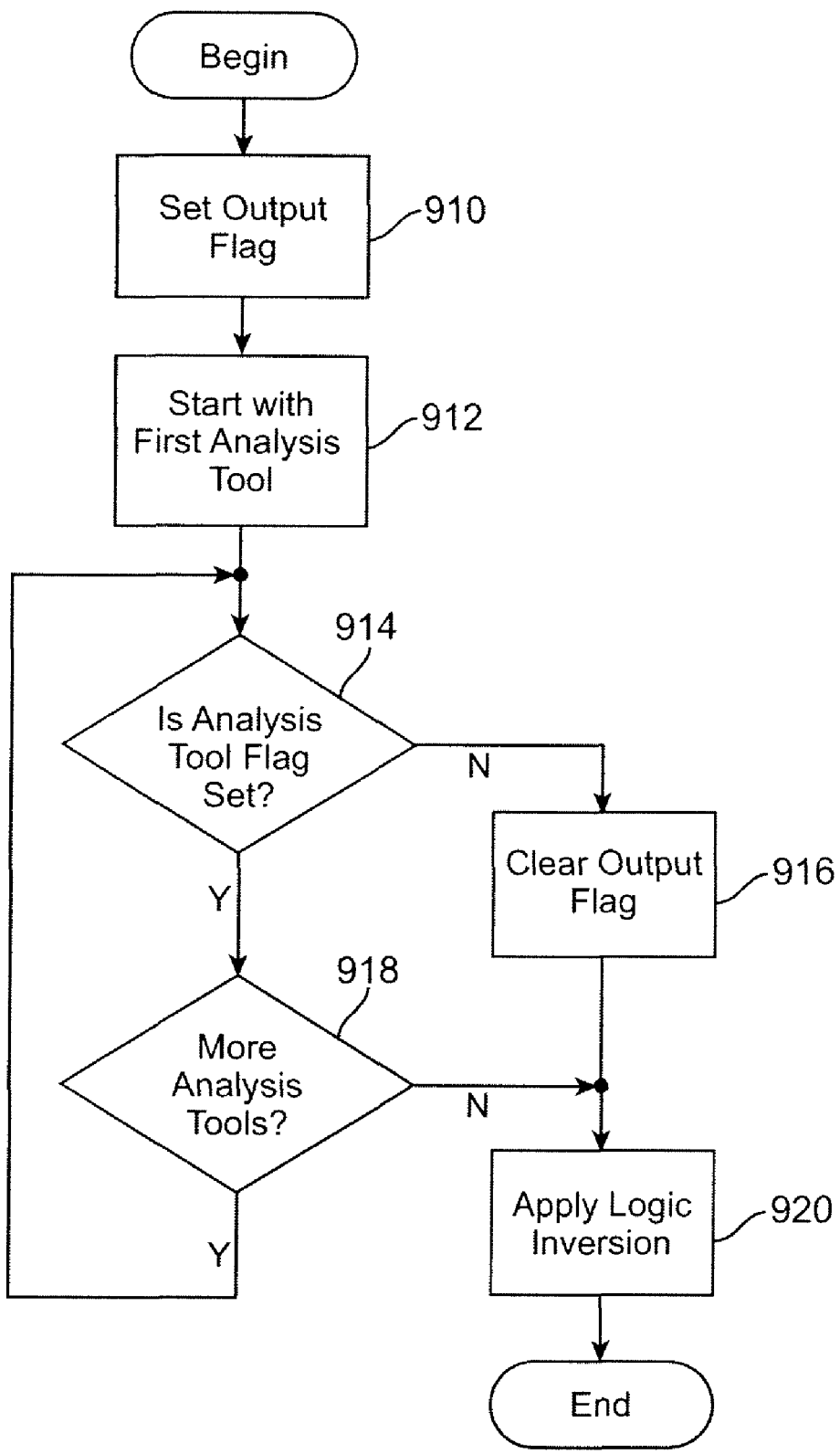
FIG. 9 is a flow chart illustrating the combination of multiple detectors including an event density detector.

In an embodiment, outputs from several analysis tools are combinable into a detection channel flag as shown in FIG. 9. Analysis tools contemplated for use in a system include line length, area, and half wave tools as described above; the event density analysis tool as described herein is another specific example. Initially an output detection channel flag is set (step 910). Beginning with the first analysis tool for a particular detection channel (step 912), if the corresponding analysis tool flag is not set (step 914), then the output detection channel flag is cleared (step 916).

If the corresponding analysis tool flag is set (step 914), the output detection channel flag remains set, and further analysis tools for the same channel, if any (step 918), are evaluated. Accordingly, this combination procedure operates as a Boolean AND operation—if any of the enabled and active analysis tools for a particular detection channel does not have a set output flag, then no detection channel flag is output by the procedure.

A clear analysis tool flag indicates that no detection has been made within the flag persistence period, and for those analysis tools that employ an X of Y criterion, that such criterion has not been met. In certain circumstances, it may be advantageous to also provide detection channel flags with logic inversion. Where a desired criterion (i.e., combination of analysis tools) is not met, the output flag is set (rather than cleared, which is the default action). This can be accomplished by providing selectable Boolean logic inversion (step 920) corresponding to each event detector.

By combining event density analysis with other detection tools, it is possible to deliver special or different types of responsive therapy within clusters of activity—when the patient's brain is especially "hot" or susceptible to events, for example, higher levels of responsive therapy may be applied. In an embodiment, the event density analysis tool by itself triggers warnings and low-frequency sine wave stimulation (described below) to attempt to reduce the patient's susceptibility to seizures; the event density tool in combination with other detections triggers increased therapy intensity.

It is recognized that therapy event density is only one type of meta-analysis capable of being combined with other detection tools. Seizure detection density, internal device measurements, and other measurable parameters may also prove to be useful parameters in this context.

Figure 10:
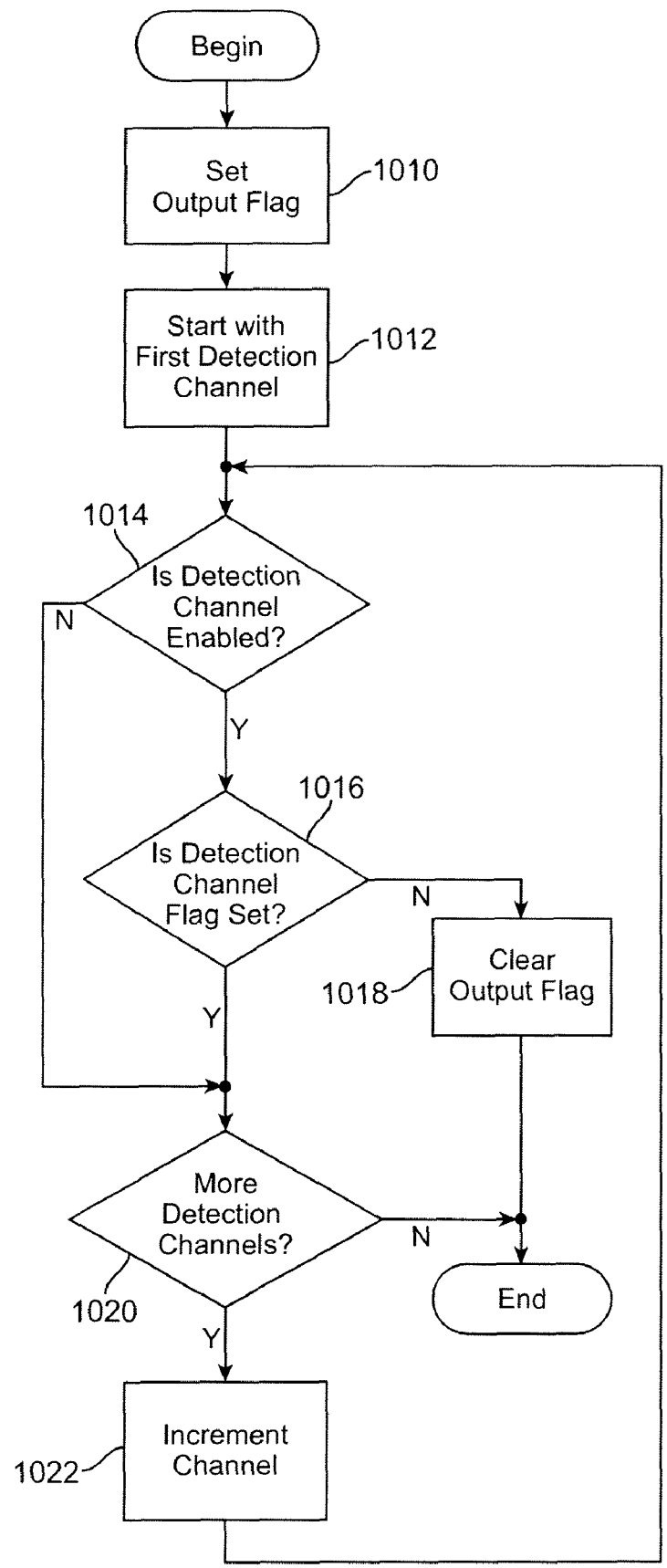
FIG. 10 is a flow chart illustrating the combination of multiple channels of detection information.

If information from more than one channel is desired, multiple detection channel flags may also be combined into a single event detector flag as shown in FIG. 10. Initially the output event detector flag is set (step 1010). Beginning with the first detection channel for a particular event detector (step 1012), if the channel is not enabled (step 1014), then no check is made. If the channel is enabled and the corresponding detection channel flag is not set (step 1016), then the output event detector flag is cleared (step 1018) and the combination procedure exits. If the corresponding detection channel flag is set (step 1016), the output event detector flag remains set, and further detection channels, if any (step 1020), are evaluated after incrementing the channel being considered (step 1022). Accordingly, this combination procedure also operates as a Boolean AND operation—if any of the enabled and active detection channels does not have a set output flag, then no event detector flag is output by the procedure. It should also be observed that a Boolean OR combination of detection channels may provide useful information in certain circumstances; a software or hardware flow chart accomplishing such a combination is not illustrated, but could easily be created by an individual of ordinary skill in digital electronic design or computer programming.

Multiple-channel combinations, as described by FIG. 10, facilitates the initiation of different actions and the application of different therapies when increased event densities are seen on multiple detection channels. A device in various embodiments may be programmed to selectively enable or disable multiple-channel combinations.

Above, it is described as advantageous to provide therapy or perform other actions when therapy event densities (and other event densities) exceed a programmed threshold. A practitioner of ordinary skill will recognize that various actions are possible. Specifically, but not by way of limitation, the patient may be alerted by an audio or somatosensory transducer; the patient or a caregiver may be alerted by sending a short-range or long-range telemetry message to an external device (such as a programmer or other interface device) and having the external device communicate a message or alert to the patient or caregiver; more responsive therapy of the same or different type may be initiated; periods of low-frequency stimulation (e.g., sinusoidal stimulation described below) may be initiated; thermal or optical stimulation may be applied to a desired portion of the patient's brain or nerves; or drug therapy may be applied (with an implanted drug pump or externally) to treat the patient. There are countless other possibilities; they will be understood by a clinician.

Figure 11:
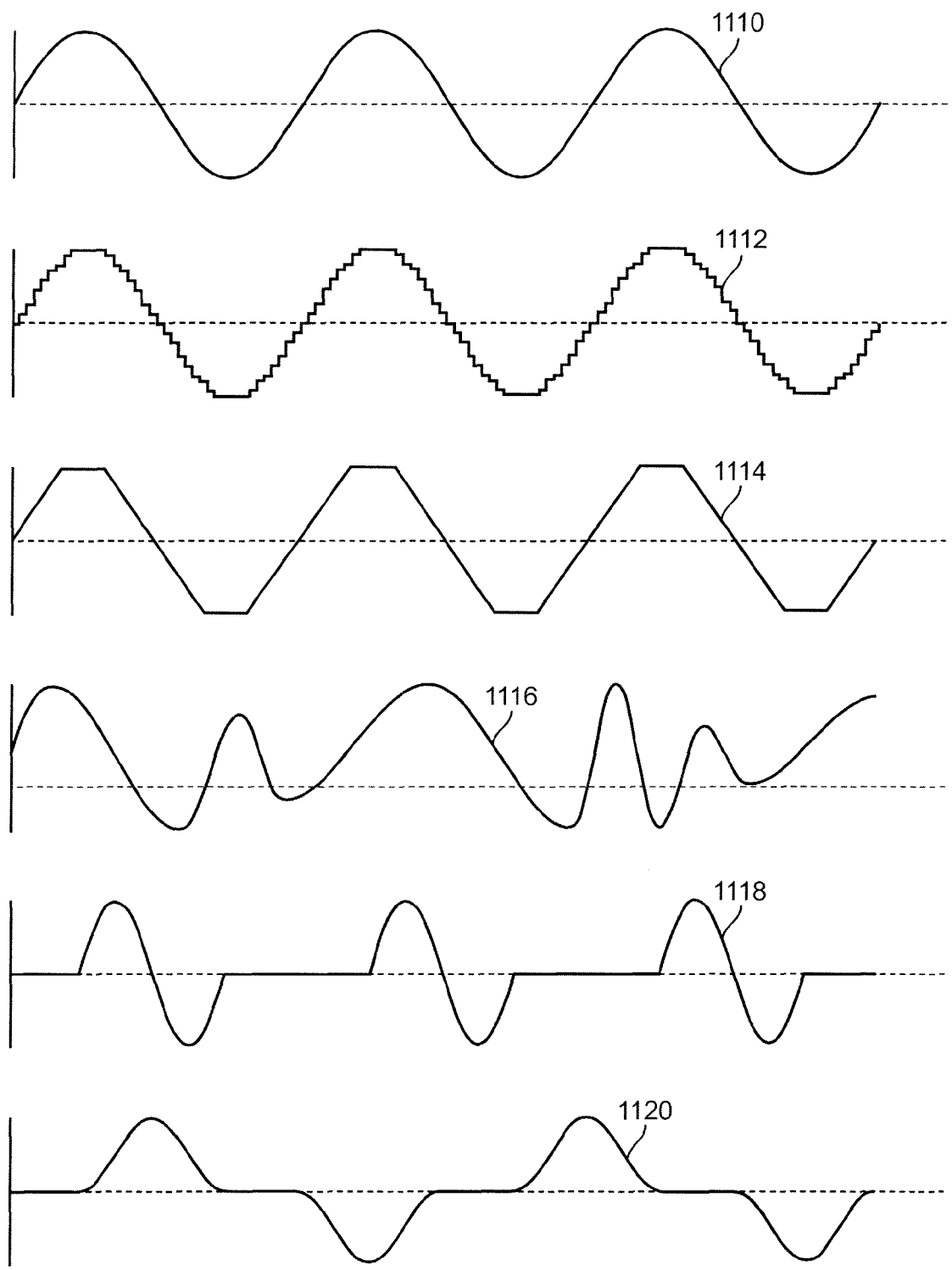
FIG. 11 illustrates several possible stimulation waveforms capable of being employed in an embodiment.

Referring now to FIG. 11, in addition to traditional biphasic pulse waveforms used for neurostimulation, other wave morphologies may have advantageous applications herein. A sinusoidal stimulation signal 1110 can be produced and used for non-responsive or responsive brain or nerve stimulation system in various embodiments. In general, sinusoidal and quasi-sinusoidal waveforms may be delivered at low frequencies to have an inhibitory effect, where low frequencies are 0.5 to 10 Hz delivered for 0.05 to 60 minutes at a time. Such waveform may be applied as a result of determining that inhibition is desired on a scheduled basis, or after conditions indicate that responsive stimulation should be applied. Higher frequency sinusoidal or quasi-sinusoidal waveforms may be used for activation. Even higher frequency sinusoidal or pulsatile stimulation may tend to simulate the effects of lesioning (but reversibly), more or less blocking the function of the target structure.

This form of stimulation is particularly advantageous for long-term treatment of enhanced susceptibility. As described above, at times a patient's epileptic brain may be essentially "hot"—prone to repeated seizures, regardless of the outcome of therapy applied directly in response to observed activity (i.e., whether stimulation was successful in preventing or terminating clinical symptoms). The longer-duration low-frequency (and generally lower-amplitude) stimulation described herein tends to treat and prevent such unstable brain states. This may result in a long-term improvement or remission in symptoms, such as a reduction in seizure frequency or severity, beyond direct results of therapy.

Amplitudes in the range of 0.1 to 10 mA would typically be used for non-pulsatile stimulation (with higher amplitudes possible for short-pulse biphasic pulsatile stimulation), but attention to safe charge densities is important to avoid neural tissue damage (where a conservative limit is 25.mu.C/cm.sup.2 per phase). It should be noted that the inhibitory and activating functions of various sinusoidal stimulation parameters may vary when applied to different parts of the brain; the above is merely exemplary.

Sinusoidal and quasi-sinusoidal waveforms presented herein would be constructed digitally by the therapy subsystem 424 (FIG. 4) of the implantable neurostimulator device 110. As a result, the sinusoid 1110 is really generated as a stepwise approximation, via a series of small steps 1112. The time between steps is dependent upon the details of the waveform being generated, but an interval on the order of 40 microseconds has been found to be a useful value. It is anticipated that the stair step waveform 1112 may be filtered to arrive at a waveform more similar to 1110, which would allow for longer periods of time between steps and larger steps. Likewise, for the waveforms 1116-1120 (described below), it is assumed that they may be created with a series of steps notwithstanding their continuous appearance in the figures.

A truncated ramp waveform 1114 is also possible, where the rate of the ramp, the amplitude reached and the dwell at the extrema are all selectable parameters. The truncated ramp has the advantage of ease of generation while providing the physiological benefits of a sinusoidal or quasi-sinusoidal waveform.

A variable sinusoidal waveform 1116 where the amplitude and frequency are varied while the waveform is applied is also illustrated. The rate and amplitude of the variation may be varied based upon a predefined plan, or may be the result of the implanted neurostimulator sensing signals from the brain during application or between applications of the waveform, and adjusting to achieve a particular change in the sensed signals. The variable waveform 1116 is illustrated herein as having a positive direct current component, but it should be noted that this waveform, as well as any of the others described herein as suitable for use, may or may not be provided with a direct current component as clinically desired.

Waveforms 1118-1120 depict variations where the stimulating waveform is generated having a largely smooth waveform, but having the additional feature where the interval between waveforms is set by varying a selectable delay, as would be used with the traditional biphasic pulse waveforms described previously. In waveform 1118, the stimulating waveforms are segments of a sine wave separated in time (of course the same technique could be used for the truncated ramp, or other arbitrary morphologies). Waveform 1120 shows a variation where the derivative in time of the waveform approaches zero as the amplitude approaches zero. The particular waveform 1120 is known as a haversine pulse.

Although the term "haversine pulse" is useful to describe the waveform of 1120, it should be noted that all of the waveforms represented in FIG. 11 are considered herein to be generally "non-pulsatile," in contrast with waveforms made up of traditional discontinuous (e.g. square) pulses. As the term is used herein, "non-pulsatile" can also be applied to other continuous, semi-continuous, discontinuous, or stepwise approximated waveforms that are not exclusively defined by monophasic or biphasic square pulses.

In the disclosed embodiment, the default stimulation behavior provided by a neurostimulator is to stimulate with charge-balanced biphasic pulses. This behavior is enforced by stimulation generation hardware that automatically generates a symmetric equal-current and equal-duration but opposite-polarity pulse as part of every stimulation pulse; the precise current control enabled in the embodiments herein makes this approach possible. However, the neurostimulator is preferably programmable to disable the automatic charge balancing pulse, thereby enabling the application of monophasic pulses (of either polarity) and other unbalanced signals.

Alternatively, if desired, charge balancing can be accomplished in software by programming the neurostimulator to specifically generate balancing pulses or signals of opposite phase. Regardless of whether charge balancing is accomplished through hardware or software, it is not necessary for each individual pulse or other waveform component to be counteracted by a signal with identical morphology and opposing polarity; symmetric signals are not always necessary. It is also possible, when charge balancing is desired, to continuously or periodically calculate the accumulated charge in each direction and ensure that the running total is at or near zero over a relatively long term and preferably, that it does not exceed a safety threshold even for a short time.

To minimize the risks associated with waveforms that are either unbalanced or that have a direct current component, it is advantageous to use electrodes having enhanced surface areas. This can be achieved by using a high surface area material like platinum black or titanium nitride as part or all of the electrode. Some experimenters have used iridium oxide advantageously for brain stimulation, and it could also be used here. See Weiland and Anderson, "Chronic Neural Stimulation with Thin-Film, Iridium Oxide Electrodes," IEEE Transactions on Biomedical Engineering, 47:911-918 (2000).

An implantable version of a system advantageously has a long-term average current consumption on the order of 10 microamps, allowing the implanted device to operate on power provided by a coin cell or similarly small battery for a period of years without need for replacement. It should be noted, however, that as battery and power supply configurations vary, the long-term average current consumption of a device may also vary and still provide satisfactory performance.

It should be observed that while the foregoing detailed description of various embodiments of the present invention is set forth in some detail, the invention is not limited to those details and an implantable neurostimulator device or system made according to the invention can differ from the disclosed embodiments in numerous ways. In particular, it will be appreciated that embodiments of the present invention may be employed in many different applications to responsively treat various chronic pain conditions. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. An implantable device for detecting a patient's increased susceptibility to neurological events and triggering an action when a state of increased susceptibility is detected, the device comprising:
 a buffer configured to store a time of a therapy event each time a therapy is delivered to the patient; and
 a central processing unit configured to select an event time window and including a therapy density analyzer, the therapy density analyzer further comprising:

a therapy event identifier configured to identify a selected therapy event that occurred in the event time window;

an interval counter configured to measure time elapsed from the time of a therapy event that is a predetermined number of therapy events prior to the selected therapy event to the time of the selected event; and a density evaluator configured to compare the time elapsed from the time of the therapy event that is the predetermined number of therapy events prior to the selected therapy event to the time of the selected event to a predetermined time interval, and if elapsed time is less than the predetermined time interval, to provide a signal that is configured to initiate one or more actions to respond to the neurological events, wherein the therapy event identifier is configured to identify another selected therapy event that occurred in the event time window if the elapsed time is not less than the predetermined time interval for the selected therapy event and if not all therapy events in the event time window have been previously selected.

2. The implantable device of claim 1, wherein each of the therapy events represents an application of a responsive electrical stimulation therapy.

3. The implantable device of claim 1, wherein the one or more actions are selected from the group consisting of: alerting the patient using an audio transducer directly or indirectly in communication with the density evaluator; alerting the patient using a somatosensory transducer directly or indirectly in communication with the density evaluator; alerting the patient using telemetry associated with the density evaluator and in operable communication with a patient alerting device; and alerting a patient's caregiver using telemetry associated with the density evaluator and in operable communication with a caregiver's alerting device.

4. The implantable device of claim 1, wherein the one or more actions comprise sending one or more signals that will cause the implantable device to change the therapy that the implantable device delivers in response to the predetermined conditions.

5. The implantable device of claim 4, wherein changing the therapy comprises changing the form of therapy from a form of pulsatile electrical stimulation to a form of nonpulsatile stimulation.

6. The implantable device of claim 5, wherein the nonpulsatile stimulation is sine wave stimulation.

7. The implantable device of claim 4, wherein changing the therapy comprises changing the form of therapy from a form of electrical stimulation to a drug therapy.

8. A method for detecting a patient's susceptibility to neurological events, the method comprising:
(a) determining a time of a therapy event each time a therapy is delivered to the patient;
(b) selecting an event time window;
(c) selecting a therapy event that occurred during the event time window;
(d) measuring time elapsed from a therapy event that is a predetermined number of therapy events prior to the selected therapy event to the selected therapy event;
(e) comparing the time elapsed from the therapy event that is the predetermined number of therapy events prior to the selected therapy event to the selected therapy event to a predetermined time interval;
(f) if the elapsed time is less than the predetermined time interval, providing a signal that is configured to initiate one or more actions to respond to the neurological events; and
(g) if the elapsed time is not less than the predetermined time interval, repeating (c), (d), (e) and (f) for each therapy event in the window unless the elapsed time is less than the predetermined time interval for said therapy event or until all therapy events in the window have been selected.

9. The method of claim 8, wherein each of the therapy events represents an application of a responsive electrical stimulation therapy.

10. The method of claim 8, wherein the one or more actions are selected from the group consisting of: alerting the patient using an audio transducer; alerting the patient using a somatosensory transducer; and alerting a patient's caregiver.

11. The method of claim 8, wherein the one or more actions comprise sending one or more signals that will cause an implantable device in the patient to change the therapy that the implantable device delivers in response to the predetermined conditions.

12. The method of claim 11, wherein changing the therapy comprises changing the form of therapy from a form of pulsatile electrical stimulation to a form of nonpulsatile stimulation.

13. The method of claim 12, wherein the nonpulsatile stimulation is sine wave stimulation.

14. The method of claim 11, wherein changing the therapy comprises changing the form of therapy from a form of electrical stimulation to a drug therapy.

* * * * *